(12) United States Patent
Klug et al.

(10) Patent No.: US 9,504,636 B2
(45) Date of Patent: Nov. 29, 2016

(54) SURFACTANT SOLUTIONS CONTAINING N-METHYL-N-OLEYLGLUCAMINES AND N-METHYL-N-$C_{12}$-$C_{14}$-ACYLGLUCAMINES

(71) Applicants: Peter Klug, Grossostheim (DE); Franz-Xaver Scherl, Burgkirchen (DE); Carina Mildner, Frankfurt am Main (DE); Eva-Maria Keitzl, Muehldorf (DE)

(72) Inventors: Peter Klug, Grossostheim (DE); Franz-Xaver Scherl, Burgkirchen (DE); Carina Mildner, Frankfurt am Main (DE); Eva-Maria Keitzl, Muehldorf (DE)

(73) Assignee: Clariant International Ltd., Muttenz (CH)

( * ) Notice: Subject to any disclaimer, the term of this patent is extended or adjusted under 35 U.S.C. 154(b) by 0 days.

(21) Appl. No.: 14/401,796

(22) PCT Filed: May 29, 2013

(86) PCT No.: PCT/EP2013/061044
§ 371 (c)(1),
(2) Date: Nov. 17, 2014

(87) PCT Pub. No.: WO2013/178668
PCT Pub. Date: Dec. 5, 2013

(65) Prior Publication Data
US 2015/0126424 A1 May 7, 2015

(30) Foreign Application Priority Data

May 30, 2012 (DE) .................. 10 2012 010 701

(51) Int. Cl.
| | | |
|---|---|---|
| C11D 3/30 | (2006.01) | |
| C11D 3/32 | (2006.01) | |
| C11D 3/43 | (2006.01) | |
| A61K 8/41 | (2006.01) | |
| A61K 8/34 | (2006.01) | |
| A61K 8/42 | (2006.01) | |
| A61Q 5/02 | (2006.01) | |
| A61Q 19/10 | (2006.01) | |

(52) U.S. Cl.
CPC . *A61K 8/41* (2013.01); *A61K 8/34* (2013.01); *A61K 8/345* (2013.01); *A61K 8/42* (2013.01); *A61Q 5/02* (2013.01); *A61Q 19/10* (2013.01); *A61K 2800/596* (2013.01)

(58) Field of Classification Search
CPC ....... C11D 3/0094; C11D 3/201; C11D 3/30; C11D 3/32; C11D 3/3917; C11D 3/43; C11D 7/261; C11D 7/3263
See application file for complete search history.

(56) References Cited

U.S. PATENT DOCUMENTS

| | | | |
|---|---|---|---|
| 5,750,748 A | 5/1998 | Boutique et al. | |
| 5,789,372 A | 8/1998 | Fabry | |
| 6,147,045 A * | 11/2000 | Lappas | 510/305 |
| 2002/0004476 A1* | 1/2002 | Pancheri | C11D 3/1233 510/509 |
| 2003/0069153 A1* | 4/2003 | Jordan et al. | 510/276 |
| 2009/0253612 A1* | 10/2009 | Mushock et al. | 512/4 |
| 2011/0251116 A1* | 10/2011 | Aehle et al. | 510/374 |
| 2014/0255330 A1* | 9/2014 | Cron et al. | 424/65 |
| 2015/0125415 A1 | 5/2015 | Klug et al. | |
| 2015/0126424 A1 | 5/2015 | Klug et al. | |
| 2015/0126616 A1 | 5/2015 | Klug et al. | |
| 2015/0133560 A1 | 5/2015 | Klug et al. | |
| 2015/0140048 A1 | 5/2015 | Klug et al. | |
| 2015/0141466 A1 | 5/2015 | Klug et al. | |
| 2015/0141508 A1 | 5/2015 | Klug et al. | |
| 2015/0150767 A1 | 6/2015 | Klug et al. | |
| 2015/0164755 A1 | 6/2015 | Klug et al. | |
| 2015/0164756 A1 | 6/2015 | Klug et al. | |
| 2015/0320037 A1 | 11/2015 | Wacker | |
| 2016/0074310 A1 | 3/2016 | Klug et al. | |
| 2016/0136072 A1 | 5/2016 | Klug et al. | |
| 2016/0143828 A1 | 5/2016 | Klug et al. | |

FOREIGN PATENT DOCUMENTS

| | | |
|---|---|---|
| EP | 0 550 637 | 7/1993 |
| EP | 0 709 449 | 5/1996 |
| WO | WO 95/17880 | 7/1995 |
| WO | WO 95/19415 | 7/1995 |
| WO | WO 2015/082062 | 6/2015 |
| WO | WO 2016/041823 | 3/2016 |

OTHER PUBLICATIONS

Friedrich Vogel: "Kosmetik aus der Sicht des Chemikers", Chemie in Unserer Zeit, No. 5, Jan. 1, 1986 (Jan. 1, 1986), pp. 156-164, XP055109030, DOI: 10.1002/ciuz.19860200504, p. 160.
International Search Report for PCT/EP2013/061044, dated May 15, 2014.
International Preliminary Report on Patentability for PCT/EP2013/061044, dated Feb. 12, 2014.

* cited by examiner

*Primary Examiner* — Charles Boyer
(74) *Attorney, Agent, or Firm* — Tod A. Waldrop

(57) ABSTRACT

The invention relates to a surfactant solution containing: (a) 28 to 65 wt.-% of a mixture of (a1) 5 to 20 wt.-% of N-methyl-N-oleylglucamine, (a2) 50 to 93 wt.-% of N-methyl-N—$C_{12}$-$C_{14}$-acylglucamines, (a3) 0 to 30 wt.-% of other N-methyl-N-acylglucamines, components (a1), (a2) and (a3) adding up to 100 wt.-%, (b) 0 to 20 wt.-% of one or more alcohols, (c) 20 to 72 wt.-% of water, and (d) 0 to 5 wt.-% of additives, components (a), (b), (c) and (d) adding up to 100 wt.-%.

8 Claims, No Drawings

SURFACTANT SOLUTIONS CONTAINING N-METHYL-N-OLEYLGLUCAMINES AND N-METHYL-N-$C_{12}$-$C_{14}$-ACYLGLUCAMINES

The invention relates to surfactant solutions comprising N-methyl-N-oleylglucamine and N-methyl-N—$C_{12}$-$C_{14}$-acylglucamines, and to cosmetic compositions comprising these N-methyl-N-acylglucamines.

It is known that short-chain sugar surfactants can be used as solubilizers or surfactants in cleaning products or cosmetic compositions.

WO 95/17880 discloses a hair shampoo composition comprising alkyl glycol ether sulfates and alkyl sulfates, and also polyhydroxyalkyl fatty acid amides. One alkyl glycol ether sulfate mentioned is lauryl triethylene glycol ether sulfate; one alkyl sulfate mentioned is lauryl sulfate. Compounds listed as polyhydroxyalkyl fatty acid amides are those of the formula

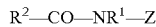

where $R^1$ is preferably $C_1$-$C_4$-alkyl, especially methyl, $R^2$ is preferably straight-chain $C_7$-$C_{19}$-alkyl or -alkenyl, especially straight-chain $C_{11}$-$C_{16}$-alkyl or -alkenyl, and Z is especially 1-deoxyglucityl, 2-deoxyfructityl, 1-deoxymaltityl, 1-deoxylactityl, 1-deoxygalactityl, 1-deoxymannityl or 1-deoxymaltotriothityl. The examples disclose hair shampoo compositions comprising ammonium lauryl sulfate, ammonium lauryl triethylene glycol sulfate and lauryl-N-methylglucamide.

WO 95/19415 discloses mixtures of a) N-acyl-N-methylglucamines having a $C_8$-$C_{10}$-acyl radical and b) N-acyl-N-methylglucamines having a $C_{12}$-$C_{18}$-acyl radical, especially a $C_{12}$-$C_{14}$-acyl radical. Components a) and b) are present in the mixtures in an a) to b) ratio of 80:20 to 20:80, especially in a ratio of 25:75 to 40:60. The surfactant mixtures are said to have improved surface-active properties and may contain further anionic, nonionic, cationic and amphoteric surfactants. Use in hair shampoos, hair lotions and foam baths is disclosed.

Glucamines are solids having melting points of about 85° C. ($C_{12}$-$C_{14}$-acylglucamines, containing 10% by weight of propylene glycol) and about 85° C. ($C_{16}$-$C_{18}$-acylglucamines, containing 20% by weight of propylene glycol). The corresponding pure substances actually have significantly higher melting points. $C_{12}$-$C_{14}$-Acylglucamines generally form sparingly water-soluble gels on dilution with water. Thus, the dilution of these N-acyl-N-methylglucamines in water down to 2% by weight solutions leads to the formation of a gel phase, which greatly complicates the handling of these surfactants.

N-Methyl-N-acylglucamines have the formula (I)

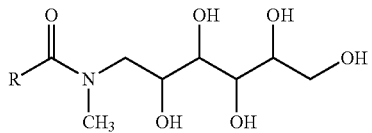

in which R is an alkyl radical or a mono- or polyunsaturated alkenyl radical.

The problem addressed by the invention is that of providing concentrated surfactant solutions comprising acylglucamines which do not cause any gel formation on dilution with water.

The problem is solved by a surfactant solution comprising
(a) 28% to 65% by weight of a mixture of (a1) 5% to 20% by weight of N-methyl-N-oleylglucamines,
(a2) 50% to 95% by weight of N-methyl-N—$C_{12}$-$C_{14}$-acylglucamines,
(a3) 0% to 30% by weight of further N-methyl-N-acylglucamines,
where the sum total of components (a1), (a2) and (a3) is 100% by weight,
(b) 0% to 20% by weight of one or more alcohols,
(c) 20% to 72% by weight of water,
(d) 0% to 5% by weight of additives,
where the sum total of components (a), (b), (c) and (d) is 100% by weight.

It has been found that a mixture of N-methyl-N-oleylglucamines and N-methyl-N—$C_{12}$-$C_{14}$-acylglucamines does not cause any gel formation on dilution with water. This means that dilute solutions produced from the inventive surfactant solutions can more easily be mixed and homogenized with the further ingredients of cosmetic compositions in the formulation process. The cosmetic compositions obtained do not have any inhomogeneities. Moreover, the stirring times in the production of the cosmetic compositions are reduced.

The inventive surfactant solutions generally have a melting point of <40° C. and are therefore pumpable in the warmed state and easy to handle on the industrial scale.

The N-methyl-N-acylglucamines present in the inventive surfactant solutions contain 5% to 20% by weight of N-methyl-N-acylglucamines containing an oleyl group. Preferably, the proportion of N-methyl-N-acylglucamines containing an oleyl group is 6% to 18% by weight, more preferably 7% to 15% by weight, based on the amount of all the N-methyl-N-acylglucamines.

In addition, the N-methyl-N-acylglucamines contain 50% to 95% by weight of N-methyl-N-acylglucamines containing a $C_{12}$-$C_{14}$-acyl group. These are derived from lauric acid and myristic acid. Preferably, this proportion is 60% to 90% by weight, more preferably 70% to 85% by weight, based on the amount of all the N-methyl-N-acylglucamines.

Furthermore, the N-methyl-N-acylglucamines present in the inventive surfactant solutions contain 0% to 30% by weight of further N-methyl-N-acylglucamines derived from short-chain and/or long-chain fatty acids, especially those which contain $C_1$-$C_4$-acyl, $C_6$-acyl, $C_8$-acyl, $C_{10}$-acyl, $C_{16}$-acyl, $C_{18}$-acyl (except for oleyl) and/or $C_{20}$-acyl. This proportion is preferably 5% to 25% by weight, more preferably 7% to 20% by weight, based on the amount of all the N-methyl-N-acylglucamines.

The N-methyl-N-acylglucamines may, as described in EP 0 550 637 B1, be prepared by reacting the corresponding fatty acid esters or fatty acid ester mixtures with N-methylglucamine in the presence of a solvent having hydroxyl groups or alkoxy groups. Suitable solvents are, for example, $C_1$-$C_4$ monoalcohols, ethylene glycol, 1,2-propylene glycol, glycerol and alkoxylated alcohols. Preference is given to 1,2-propylene glycol. N-Methylglucamine can, as likewise described in EP 0 550 637 A1, be obtained by reductive amination of glucose with methylamine.

Suitable fatty acid esters which are reacted with the N-methylglucamines to give N-methyl-N-acylglucamines are generally the methyl esters, which are obtained by transesterification from natural fats and oils, for example the triglycerides.

Suitable raw materials for the preparation of the fatty acid methyl esters are, for example, coconut oil or palm oil.

In addition, the inventive surfactant solutions may comprise, as component (b), one or more alcohols. Suitable alcohols are water-miscible monoalcohols or diols. Preference is given to ethanol, 1,2-propylene glycol, glycerol, 1,3-propylene glycol and isopropanol.

In a preferred embodiment of the invention, the surfactant solutions do not include any monoalcohol. They may, however, contain dials such as 1,2-propylene glycol.

The following may be present as additives in the inventive surfactant solutions: preservatives, complexing agents and neutralizing agents, and buffers, for example citric acid or citric salts.

In a preferred embodiment, the inventive surfactant solution comprises
(a) 30% to 65% by weight of a mixture of
  (a1) 6% to 18% by weight of N-methyl-N-oleylglucamine,
  (a2) 60% to 75% by weight of N-methyl-N—$C_{12}$-$C_{14}$-acylglucamines,
  (a3) 10% to 30% by weight of further N-methyl-N-acylglucamines,
  where the sum total of components (a1), (a2) and (a3) is 100% by weight,
(b) 3% to 17% by weight of one or more alcohols,
(c) 25% to 67% by weight of water,
(d) 0% to 2% by weight of additives,
where the sum total of components (a), (b), (c) and (d) is 100% by weight.

The invention also provides for the use of the surfactant solutions for production of cosmetic compositions.

The production of the cosmetic compositions comprises the step of diluting the surfactant solutions with water. In general, the inventive surfactant solutions are diluted with water in a ratio of 1:1 to 1:50, preferably 1:2 to 1:10. In general, the surfactant solutions are diluted to such an extent that the final concentration of the N-methyl-N-acylglucamines is in the range from 1% to 10% by weight, preferably in the range from 2% to 5% by weight.

The invention also provides concentrated compositions comprising
(A) 25% to 60% by weight of a mixture of
  (a1) 5% to 20% by weight, preferably 6% to 18% by weight, of N-methyl-N-oleylglucamine,
  (a2) 50% to 95% by weight, preferably 60% to 75% by weight, of N-methyl-N—$C_{12}$-$C_{14}$-acylglucamines,
  (a3) 0% to 30% by weight, preferably 10% to 30% by weight, of further N-methyl-N-acylglucamines,
  where the sum total of components (a1), (a2) and (a3) is 100% by weight, as component (A),
(B) 0% to 10% by weight of one or more further surfactants as component (B),
(C) 0% to 20% by weight of one or more alcohols as component (C),
(D) 20% to 72% by weight of water as component (D),
(E) 0% to 5% by weight of further auxiliaries and additives as component (E),
where the sum total of components (A), (B), (C), (D) and (E) is 100% by weight.

The compositions preferably comprise
(A) 25% to 60% by weight of component (A),
(B) 1% to 5% by weight of component (B),
(C) 3% to 17% by weight of component (C),
(D) 25% to 65% by weight of component (D),
(E) 0% to 2% by weight of component (E),
where the sum total of components (A), (B), (C), (D) and (E) is 100% by weight.

The further surfactants (B) may be nonionic surfactants, anionic surfactants, cationic surfactants and betaine surfactants.

Useful anionic surfactants include ($C_{10}$-$C_{22}$)-alkyl and -alkylene carboxylates, alkyl ether carboxylates, fatty alcohol sulfates, fatty alcohol ether sulfates, alkylamide sulfates and sulfonates, fatty acid alkylamide polyglycol ether sulfates, alkanesulfonates and hydroxyalkanesulfonates, olefinsulfonates, acyl esters of isethionates, alpha-sulfo fatty acid esters, alkylbenzenesulfonates, alkylphenol glycol ether sulfonates, sulfosuccinates, sulfosuccinic monoesters and diesters, fatty alcohol phosphates, fatty alcohol ether phosphates, protein-fatty acid condensation products, alkyl monoglyceride sulfates and sulfonates, alkyl glyceride ether sulfonates, fatty acid methyl taurides, fatty acid sarcosinates, sulfosuccinates, sulforicinoleates, acylglutamates and acylglycinates. These compounds and mixtures thereof are utilized in the form of their water-soluble or water-dispersible salts, for example the sodium, potassium, magnesium, ammonium, mono-, di- and triethanolammonium and the analogous alkylammonium salts.

In one embodiment of the invention, the compositions comprise one or more anionic surfactants from the group of the alkyl sulfates and alkyl ether sulfates.

Preferred alkyl sulfates are the $C_8$-$C_{20}$-alkyl sulfates, especially the linear $C_8$-$C_{20}$-alkyl sulfates in the form of their sodium, potassium or ammonium salts. Examples of alkyl sulfates are lauryl sulfate, cocoalkyl sulfate and tallowalkyl sulfate. Particular preference is given to lauryl sulfate.

Preferred alkyl ether sulfates are the $C_8$-$C_{20}$-alkyl ether sulfates, particular preference being given to the linear $C_8$-$C_{20}$-alkyl ether sulfates, especially the alkyl glycol ether sulfates derived from the ethoxylated fatty alcohols, in the form of their sodium, potassium or ammonium salts. Examples of alkyl ether sulfates are lauryl ether sulfate, cocoalkyl ether sulfate and tallowalkyl ether sulfate. Examples of glycol ether sulfates are lauryl triethylene glycol ether sulfate, cocoalkyl triethylene glycol ether sulfate and tallowalkyl hexaethylene glycol ether sulfate. Lauryl glycol ether sulfate is especially preferred, for example lauryl triethylene glycol ether sulfate.

Betaine surfactants contain, in the same molecule, a cationic group, especially an ammonium group, and an anionic group, which may be a carboxylate group, sulfate group or sulfonate group. Suitable betaines are alkyl betaines such as cocobetaine or fatty acid alkylamidopropyl betaines, for example cocoacylamidopropyl dimethyl betaine, $C_{12}$-$C_{18}$ dimethylamino-hexanoates or $C_{10}$-$C_{18}$ acylamidopropane dimethyl betaines.

In a preferred embodiment of the invention, the compositions comprise one or more amidopropyl betaines of the formula (I)

$$R^a\underset{H}{\overset{O}{\underset{\|}{C}}}-N-CH_2CH_2CH_2-\overset{CH_3}{\underset{CH_3}{N^+}}-CH_2-\underset{O^-}{\overset{O}{\underset{\|}{C}}} \quad (I)$$

in which $R^a$ is a linear or branched saturated $C_7$-$C_{21}$-alkyl group or a linear or branched mono- or polyunsaturated $C_7$-$C_{21}$-alkenyl group.

In a further preferred embodiment of the invention, the compositions comprise one or more betaines of the formula (II)

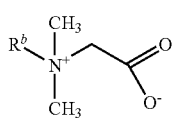

(II)

in which $R^b$ is a linear or branched saturated $C_8$-$C_{22}$-alkyl group or a linear or branched mono- or polyunsaturated $C_8$-$C_{22}$-alkenyl group.

In a further preferred embodiment of the invention, the compositions comprise one or more sulfo betaines of the formula (III)

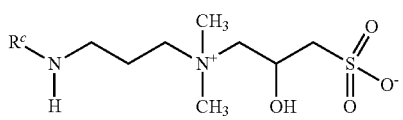

(III)

in which $R^c$ is a linear or branched saturated $C_8$-$C_{22}$-alkyl group or a linear or branched mono- or polyunsaturated $C_8$-$C_{22}$-alkenyl group.

More preferably, the compositions comprise one or more betaine surfactants selected from the group of the compounds consisting of the amidopropyl betaines of the formula (I), the betaines of the formula (II) and the sulfo betaines of the formula (III).

In an especially preferred embodiment of the invention, the compositions comprise one or more betaine surfactants selected from the amidopropyl betaines of the formula (I).

In a further especially preferred embodiment of the invention, the compositions comprise one or more betaine surfactants selected from the betaines of the formula (II).

In a further especially preferred embodiment of the invention, the compositions comprise one or more betaine surfactants selected from the sulfo betaines of the formula (III).

Preferably, the $R^a$ radical in the one or more amidopropyl betaines of the formula (I) is a linear or branched saturated $C_7$-$C_{17}$-alkyl group. Among the linear and branched saturated alkyl groups $R^a$, preference is given to the linear saturated alkyl groups.

More preferably, the amidopropyl betaines of the formula (I) are cocamidopropyl betaines.

Preferably, the $R^b$ radical in the one or more betaines of the formula (II) is a linear or branched saturated $C_8$-$C_{18}$-alkyl group and more preferably a linear or branched saturated $C_{12}$-$C_{18}$-alkyl group. Among the linear and branched saturated alkyl groups $R^b$, preference is given to the linear saturated alkyl groups.

Preferably, the $R^c$ radical in the one or more sulfo betaines of the formula (III) is a linear or branched saturated $C_8$-$C_{18}$-alkyl group and more preferably a linear or branched saturated $C_{12}$-$C_{18}$-alkyl group. Among the linear and branched saturated alkyl groups $R^c$, preference is given to the linear saturated alkyl groups.

More preferably, the aqueous surfactant solutions comprise amidopropyl betaines of the formula (I) and/or alkyl betaines of the formula (II).

Preferably, the compositions comprise, as well as the anionic surfactant, a betaine surfactant.

More preferably, the compositions comprise the above-described alkyl sulfates and/or alkyl ether sulfates and betaine surfactants.

Suitable cationic surfactants are substituted or unsubstituted, straight-chain or branched quaternary ammonium salts of the $R^1N(CH_3)_3X$, $R^1R^2N(CH_3)_2X$, $R^1R^2R^3N(CH_3)X$ or $R^1R^2R^3R^4NX$ type. The $R^1$, $R^2$, $R^3$ and $R^4$ radicals may preferably each independently be unsubstituted alkyl having a chain length between 8 and 24 carbon atoms, especially between 10 and 18 carbon atoms, hydroxyalkyl having 1 to 4 carbon atoms, phenyl, $C_2$- to $C_{18}$-alkenyl, $C_7$- to $C_{24}$-aralkyl, $(C_2H_4O)_xH$ where x is from 1 to 3, alkyl radicals containing one or more ester groups, or cyclic quaternary ammonium salts. X is a suitable anion. Preference is given to $(C_8$-$C_{22})$-alkyltrimethylammonium chloride or bromide, more preferably cetyltrimethylammonium chloride or bromide, di-$(C_8$-$C_{22})$-alkyldimethylammonium chloride or bromide, $(C_8$-$C_{22})$-alkyldimethylbenzylammonium chloride or bromide, $(C_8$-$C_{22})$-alkyldimethylhydroxyethylammonium chloride, phosphate, sulfate, lactate, more preferably distearyldimethylammonium chloride, di-$(C_8$-$C_{22})$-alkylamidopropyltrimethylammonium chloride and methosulfate.

Examples of useful nonionic surfactants include the following compounds:

Polyethylene oxide, polypropylene oxide and polybutylene oxide condensates of alkylphenols. These compounds comprise the condensation products of alkylphenols having a $C_6$- to $C_{20}$-alkyl group which may be either linear or branched with alkene oxides. These surfactants are referred to as alkylphenol alkoxylates, e.g. alkylphenol ethoxylates.

Condensation products of aliphatic alcohols with 1 to 25 mol of ethylene oxide. The alkyl or alkenyl chain of the aliphatic alcohols may be linear or branched, primary or secondary, and contains generally 8 to 22 carbon atoms. Particular preference is given to the condensation products of $C_{10}$ to $C_{20}$ alcohols with 2 to 18 mol of ethylene oxide per mole of alcohol. The alcohol ethoxylates may have a narrow ("narrow range ethoxylates") or a broad homolog distribution of the ethylene oxide ("broad range ethoxylates"). Examples of commercially available nonionic surfactants of this type are Tergitol® 15-S-9 (condensation product of a linear secondary $C_{11}$-$C_{15}$ alcohol with 9 mol of ethylene oxide), Tergitol® 24-L-NMW (condensation product of a linear primary $C_{12}$-$C_{14}$ alcohol with 6 mol of ethylene oxide, having narrow molar mass distribution). This product class likewise includes the Genapol® brands from Clariant.

Condensation products of ethylene oxide with a hydrophobic basis, formed by condensation of propylene oxide with propylene glycol. The hydrophobic moiety of these compounds preferably has a molecular weight between 1500 and 1800. The addition of ethylene oxide onto this hydrophobic moiety leads to an improvement in the water solubility. The product is liquid up to a polyoxyethylene content of about 50% of the total weight of the condensation product, which corresponds to a condensation with up to about 40 mol of ethylene oxide. Commercially available examples of this product class are the Pluronic® brands from BASF and the Genapol® PF brands from Clariant.

Condensation products of ethylene oxide with a reaction product of propylene oxide and ethylenediamine. The hydrophobic unit of these compounds consists of the reaction product of ethylenediamine with excess propylene oxide and generally has a molecular weight of 2500 to 3000. Ethylene oxide is added onto this hydrophobic unit up to a content of 40 to 80% by weight of polyoxyethylene and a molecular weight of 5000 to 11 000. Commercially available examples of this compound class are the Tetronic® brands from BASF and the Genapol® PN brands from Clariant.

Further suitable nonionic surfactants are alkyl and alkenyl oligoglycosides and fatty acid polyglycol esters or fatty amine polyglycol esters each having 8 to 20 and preferably 12 to 18 carbon atoms in the fatty alkyl radical, alkyl oligoglycosides, alkenyl oligoglycosides and fatty acid N-alkylglucamines.

In addition, the inventive surfactant solutions may comprise, as component (C), one or more alcohols which originate from the inventive surfactant solution. Suitable alcohols are the abovementioned water-miscible alcohols. In a preferred embodiment of the invention, the compositions do not contain any monoalcohols.

Auxiliaries and additives (E) are, for example, preservatives, fragrances, dyes and refatting agents.

Suitable preservatives of the preservatives listed in the relevant annex of the European cosmetics legislation, for example phenoxyethanol, benzyl alcohol, parabens, benzoic acid and sorbic acid; a particularly suitable example is 1,3-bis(hydroxymethyl)-5,5-dimethylimidazolidine-2,4-dione (Nipaguard® DMDMH).

The amount of the preservatives in the inventive compositions is generally from 0% to 2% by weight, based on the total weight of the finished compositions.

In a further embodiment of the invention, the inventive compositions are in the form of concentrates for production of products for hair washing and skin cleansing, such as hair shampoos, shower gels, hand soaps and face cleansers.

The invention is illustrated in detail by the examples which follow.

EXAMPLES

Examples 1 to 4 and Comparative Example 1

The N-acyl-N-methylglucamines described hereinafter were prepared according to EP 0 550 637 from the corresponding fatty acid methyl esters or triglycerides and N-methylglucamine in the presence of 1,2-propylene glycol as solvent, and were obtained in solid form consisting of active substance and 1,2-propylene glycol (all figures in % by weight).

TABLE 1

| Preparation example | Methyl ester | Triglyceride | Active substance (%) | 1,2-Propylene glycol (%) | Melting point (° C.) |
|---|---|---|---|---|---|
| 1 | C12/14 (C12: 70%, C14: 30%) | — | 90 | 10 | 85 |
| 2 | | Coconut oil (C8: 6%; C10: 6%; C12: 48%; C14: 20%; C16: 10%; C18: 2%; C18': 8%) | 82 | 10 (+8% glycerol) | 50 |
| 3 | Coconut fatty acid methyl ester (C8: 6%; C10: 6%; C12: 48%; C14: 20%; C16: 10%; C18: 2%; C18': 8%) | | 90 | 10 | 75 |

C18 = stearic acid methyl ester;
C18' = oleic acid methyl ester

The above products are difficult to handle and have melting points greater than 50° C. They were therefore diluted with water and ethanol in order to be handleable in liquid form below 50° C. (all figures in % by weight).

TABLE 2

| Example | Glucamide according to | Active content of glucamines | Water | Ethanol | Propylene glycol | Melting point of the surfactant mixture (° C.) | 10% in water | 5% in water | 2% in water |
|---|---|---|---|---|---|---|---|---|---|
| Comparative example 1 | Preparation example 1 | 60 | 23 | 10 | 7 | 40 | white gel | white gel | gel/liquid |
| Example 1 | Preparation example 2 | 60 | 20 | 10 | 7 (+3% glycerol) | 32.5 | clear liquid about 100 mPas | clear liquid | clear liquid |
| Example 2 | Preparation example 2 | 30 | 65 | 0 | 3 (+2% glycerol) | 35 | clear liquid about 100 mPas | clear liquid | clear liquid |
| Example 3 | Preparation example 3 | 55 | 28 | 10 | 7 | 32.5 | clear liquid about 1000 mPas | clear liquid about 100 mPas | clear liquid |
| Example 4 | Preparation example 3 | 30 | 37 | 0 | 3 | 38 | clear liquid about 1000 mPas | clear liquid about 100 mPas | clear liquid |

As apparent from table 2, the inventive compositions of examples 1 to 4, in contrast to the composition according to comparative example 1, do not just have good handleability, but are also dilutable in water easily and without gel formation.

The invention claimed is:

1. A surfactant solution consisting of
   (a) 28% to 65% by weight of a mixture of
      (a1) 5% to 20% by weight of N-methyl-N-oleylglucamine,
      (a2) 50% to 93% by weight of N-methyl-N—$C_{12}$-$C_{14}$-acylglucamines,
      (a3) 0% to 30% by weight of further N-methyl-N-acylglucamines,
      where the sum total of components (a1), (a2) and (a3) is 100% by weight,
   (b) 0% to 20% by weight of one or more alcohols,
   (c) 20% to 72% by weight of water,
   (d) 0% to 5% by weight of additives,
   wherein the surfactant solution has a melting point of less than 40° C. and does not form a gel on dilution with water.

2. The surfactant solution as claimed in claim 1, wherein component (b), is selected from the group consisting of ethanol, isopropanol, 1,2-propylene glycol, 1,3-propylene glycol and glycerol.

3. The surfactant solution as claimed in claim 1, consisting of
   (a) 30% to 65% by weight of a mixture of
      (a1) 6% to 18% by weight of N-methyl-N-oleylglucamine,
      (a2) 60% to 75% by weight of N-methyl-N—$C_{12}$-$C_{14}$-acylglucamines,
      (a3) 10% to 30% by weight of further N-methyl-N-acylglucamines,
      where the sum total of components (a1), (a2) and (a3) is 100% by weight,
   (b) 3% to 17% by weight of one or more alcohols,
   (c) 25% to 67% by weight of water,
   (d) 0% to 2% by weight of additives.

4. The surfactant solution as claimed in claim 1, which does not consist of any monoalcohol.

5. A cosmetic composition comprising a surfactant solution as claimed in claim 1.

6. A process for producing cosmetic compositions, comprising the step of diluting the surfactant solution as claimed in claim 1, with water and not forming a gel.

7. A composition consisting of
   (A) 25% to 60% by weight of a mixture of
      (a1) 5% to 20% by weight of N-methyl-N-oleylglucamine,
      (a2) 50% to 95% by weight of N-methyl-N—$C_{12}$-$C_{14}$-acylglucamines,
      (a3) 0% to 30% by weight of further N-methyl-N-acylglucamines,
      where the sum total of components (a1), (a2) and (a3) is 100% by weight, as component (A),
   (B) 0% to 10% by weight of one or more further surfactants as component (B),
   (C) 0% to 20% by weight of one or more alcohols as component (C),
   (D) 20% to 72% by weight of water as component (D),
   (E) 0% to 5% by weight of further auxiliaries and additives as component (E).

8. The composition as claimed in claim 7, consisting of
   (a) 25% to 60% by weight of component (A),
   (b) 1% to 5% by weight of component (B),
   (c) 3% to 17% by weight of component (C),
   (d) 25% to 65% by weight of component (D),
   (e) 0% to 2% by weight of component (E).

* * * * *